(12) United States Patent
Sun et al.

(10) Patent No.: US 11,779,373 B2
(45) Date of Patent: Oct. 10, 2023

(54) WEARABLE ROBOT FOR INTEGRATED FRACTURE REDUCTION AND REHABILITATION

(71) Applicant: TIANJIN UNIVERSITY, Tianjin (CN)

(72) Inventors: Tao Sun, Tianjin (CN); Zhiyuan He, Tianjin (CN); Panfeng Wang, Tianjin (CN); Binbin Lian, Tianjin (CN); Yimin Song, Tianjin (CN)

(73) Assignee: TIANJIN UNIVERSITY, Tianjin (CN)

(*) Notice: Subject to any disclaimer, the term of this patent is extended or adjusted under 35 U.S.C. 154(b) by 0 days.

(21) Appl. No.: 17/428,578

(22) PCT Filed: Aug. 26, 2020

(86) PCT No.: PCT/CN2020/111417
§ 371 (c)(1),
(2) Date: Aug. 4, 2021

(87) PCT Pub. No.: WO2021/232605
PCT Pub. Date: Nov. 25, 2021

(65) Prior Publication Data
US 2023/0074130 A1 Mar. 9, 2023

(30) Foreign Application Priority Data

May 18, 2020 (CN) .......................... 202010421526.2

(51) Int. Cl.
*A61B 17/66* (2006.01)
*A61B 34/30* (2016.01)
*B25J 9/00* (2006.01)

(52) U.S. Cl.
CPC .............. *A61B 17/66* (2013.01); *A61B 34/30* (2016.02); *B25J 9/0009* (2013.01)

(58) Field of Classification Search
CPC ......... A61B 17/66; A61B 34/30; B25J 9/0009
(Continued)

(56) References Cited

U.S. PATENT DOCUMENTS

| 5,180,380 A | * | 1/1993 | Pursley | .................. A61B 17/60 606/56 |
| 6,030,386 A | * | 2/2000 | Taylor | .................... A61B 17/62 606/56 |

(Continued)

FOREIGN PATENT DOCUMENTS

| CN | 108742804 A | 11/2018 |
| CN | 109077785 A | 12/2018 |

(Continued)

OTHER PUBLICATIONS

International Search Report of PCT/CN2020/111417.

*Primary Examiner* — Eduardo C Robert
*Assistant Examiner* — David C Comstock
(74) *Attorney, Agent, or Firm* — Dragon Sun Law Firm, PC; Nathaniel Perkins

(57) ABSTRACT

A wearable robot for integrated fracture reduction and rehabilitation, comprising a proximal ring, a distal ring, six driving branch chains, motor driving device and manual driving device; the six driving branch chains are divided into two groups, each of them comprises a platform connecting sleeve, a sliding bearing, a bearing locking nut, a proximal Hooke hinge, an intermediate prismatic pair, a sleeve, a force sensor, and a distal Hooke hinge; one end of the driving branch chain is connected with the proximal ring by a connecting sleeve fastener, and the other end is connected with the distal ring by nut, each driving branch chain is connected with the driving devices via D-shaped shaft sleeve. The wearable robot has electric-manual dual model driving, and the branch chain can be quickly replaced during and after the operation.

8 Claims, 8 Drawing Sheets

(58) Field of Classification Search
USPC .............................................. 606/56, 57, 58
See application file for complete search history.

(56) References Cited

U.S. PATENT DOCUMENTS

| | | | |
|---|---|---|---|
| 8,864,750 B2* | 10/2014 | Ross | ....................... B25B 23/14 606/1 |
| 2002/0010465 A1* | 1/2002 | Koo | ....................... A61B 17/62 606/57 |
| 2014/0276821 A1 | 9/2014 | Murray et al. | |
| 2015/0080892 A1* | 3/2015 | Lehmann | ............... A61B 17/66 606/57 |
| 2016/0022314 A1* | 1/2016 | Bordeaux | .......... A61B 17/6416 606/56 |

FOREIGN PATENT DOCUMENTS

| | | | |
|---|---|---|---|
| CN | 109745107 A | 5/2019 | |
| CN | 109758218 A | 5/2019 | |

* cited by examiner

WEARABLE ROBOT FOR INTEGRATED FRACTURE REDUCTION AND REHABILITATION

CROSS-REFERENCE TO RELATED APPLICATIONS

This Application is a national stage application of PCT/CN2020/111417. This application claims priorities from PCT Application No. PCT/CN2020/111417, filed Aug. 26, 2020, and from the Chinese patent application 2020104215262 filed May 18, 2020, the content of which are incorporated herein in the entirety by reference.

TECHNICAL FIELD

The invention relates to a medical instrument, in particular to a wearable robot for integrated fracture reduction and rehabilitation.

BACKGROUND OF THE PRESENT INVENTION

The traditional fracture surgery is limited by a physician's experience and intraoperative equipment, and has the disadvantages of high surgical risk, serious trauma, difficult popularization of the complex surgical method and the like, and is prone to the occurrence of inaccurate reduction, secondary infection, and the like.

According to the wearable orthopedic medical robot, a semi-spiral pin or a Kirschner wire is used for stably fixing a fractured bone with a robot distal ring and a robot proximal ring, the relative spatial posture of the robot distal ring and the robot proximal ring is adjusted to adjust the broken end of the fractured bone, and accurate and minimally invasive fracture treatment is realized. However, at present, most wearable orthopedic medical robots mainly have the following defects: 1) single driving mode. According to the six-degree-of-freedom parallel robot disclosed by the patent CN101847182A, long bone fracture reduction can be realized, but the driving mode thereof is single and cannot be dismantled, which increases the burden of a patient to a certain extent and brings inconvenience to daily life. 2) The branch chain is not replaceable. The femoral shaft fracture reduction operation can be realized by the Master-slave robot as disclosed in the patent CN106361441A, however, the branch chain structure of the robot cannot be dismantled and replaced, so that the use requirement of replacing the branch chain for a special fracture type cannot be met. 3) The overall structure is heavy and not compact, and the wearability is poor. The wearable auxiliary bone parallel robot disclosed in the patent CN101474090A can perform fracture plastic reduction and fixation simultaneously, but the driving and transmission structure is heavy, the overall arrangement form is not compact, the wearability is poor, and the wearability is not suitable for long-term use of patients in daily activities. 4) Only aiming at fracture reduction, fracture rehabilitation has not been involved. The long bone reduction robot as disclosed in the patent CN103462674A can realize long bone fracture reduction, but lacks real-time monitoring on the force information of the robot, so that the degree of bone healing is difficult to be judged to reasonably guide the rehabilitation training.

SUMMARY OF THE PRESENT INVENTION

The invention aims to overcome the defects of the prior art, and provides an orthopedic medical robot with light weight, high rigidity, strong wearability, and the integration of fracture reduction and rehabilitation, having electric-manual dual model and replaceable branch chains, so as to realize accurately and minimally invasive, safe and controllable fracture treatment.

The wearable robot for integrated fracture reduction and rehabilitation of the present invention comprises a proximal ring and a distal ring provided below the proximal ring, wherein the proximal ring and the distal ring are connected through six driving branch chains, the proximal ring and the distal ring both comprise annular bodies and are in a central symmetrical structure, flanges are formed on the annular bodies of the proximal ring and the distal ring by protruding outwards at outer edges of the annular bodies every 120°, two installing holes for connecting the driving branch chain are formed at the outer side of each flange in a vertical direction, and a plurality of round holes with axes provided along the vertical direction is uniformly spaced on the inner side of the proximal ring and the distal ring along a circumferential direction respectively.

The six driving branch chains are identical in structure, the six driving branch chains are divided into two groups according to different included angles with a symmetrical central line of the proximal ring, the included angles between two groups of driving branch chains and the symmetrical central line of the proximal ring are equal in magnitude and opposite in direction, and each group of the driving branch chains is uniformly distributed in space by taking the symmetrical central line of the proximal ring as a central axis.

One end is connected with two installing holes of any group of installing holes on the proximal ring, and the other end of the two driving branch chains is connected with two installing holes adjacent to each other in two groups of installing holes on the distal ring.

Each of the driving branch chains comprises a platform connecting sleeve, the platform connecting sleeve comprises a lower annular cylinder and an upper annular cylinder which are provided as an integrated upper and lower structure with a same axial line, one supporting arm is provided at a reducing position of the lower annular cylinder and the upper annular cylinder along a horizontal direction, a directional shaft with an axis thereof provided along the vertical direction is provided on the supporting arm, the upper annular cylinder of the platform connecting sleeve is inserted into one installing hole of the proximal ring, the upper annular cylinder is in threaded connection with a central threaded through-hole of a connecting sleeve fastener through an external thread provided on an outer wall of the upper annular cylinder, the connecting sleeve fastener is provided as being tightly pressed on a top wall of the proximal ring, and the directional shaft is inserted into an round hole on the inner side of the proximal ring to limit an axial rotation of the platform connecting sleeve.

A proximal Hooke hinge and a distal Hooke hinge comprise a central cross structure, the central cross structure comprises a Hooke hinge central block, a first through-hole and a second through-hole are respectively formed in a middle of the Hooke hinge central block along a cross direction, one long shaft is rotatably connected with the first through-hole, a stud sequentially passes through an axial through-hole in a first short shaft, a radial through-hole in a radial middle of the long shaft and an axial through-hole in the second short shaft, and the first short shaft and the second short shaft are respectively in rotating fit with the second through-hole; outer ends of the first short shaft and the second short shaft are respectively inserted into the through-holes of a left connecting arm and a right connecting arm of an U-shaped second connecting seat, the first short shaft and the second short shaft are in rotating fit with the through-holes of the left connecting arm and the right connecting arm of the second connecting seat, the first short shaft and the second short shaft are tightly pressed on a side wall of the long shaft through nuts and gaskets which are in threaded connection with two ends of the stud, two ends of the long shaft are respectively inserted into the through-holes of the left connecting arm and the right connecting arm of the U-shaped first connecting seat, the long shaft is in rotating fit with the through-holes of the left connecting arm and the right connecting arm of the first connecting seat, and the top wall of the first connecting seat of the proximal Hooke hinge is an annular wall.

One shaft rod is fixed at a center of a top surface of the first connecting seat of the proximal Hooke hinge, a lower part of the shaft rod is a cylindrical shaft section, a middle part of the shaft rod being a threaded shaft section and an upper part of the shaft rod being a D-shaped shaft section, the shaft rod sequentially passes through the central hole of a bearing locking nut and the central threaded through-hole of a sliding bearing from bottom to top, the threaded shaft section in the middle of the shaft rod is in threaded connection and fixation with the central threaded through-hole of the sliding bearing, the bearing locking nut is sleeved on the cylindrical shaft section, and a diameter of the central hole of the bearing locking nut is larger than that of the cylindrical shaft section of the lower part of the shaft rod.

The bearing locking nut and the sliding bearing are embedded into the central hole of the lower annular cylinder of the platform connecting sleeve, the bearing locking nut is in threaded fixation and connection with the inner thread of the central hole of the lower annular cylinder through the outer thread provided on the outer wall of the bearing locking nut, the sliding bearing is in rotating fit with the central hole of the lower annular cylinder, the lower end of one D-shaped shaft sleeve passes through the central hole of the upper annular cylinder of the platform connecting sleeve and is tightly sleeved on the D-shaped shaft section at the upper part of the shaft rod, and the D-shaped shaft sleeve is in clearance fit with the central hole of the upper annular cylinder of the platform connecting sleeve.

One intermediate prismatic pair comprises a lead screw or a ball screw and a flange nut connected to the lead screw or the ball screw through a lead screw pair, one end of the lead screw or the ball screw is in threaded connection with a threaded hole in the middle of a bottom surface of a second connecting seat on the proximal Hooke hinge and fixed through a nut, a sleeve is in threaded connection with the flange nut, the side wall of the sleeve is provided with a sliding groove along the axial direction of the sleeve, the other end of the lead screw or the ball screw is connected with an indicating rod, the indicating rod is inserted into the sliding groove and can move along the sliding groove, scales are marked on the outer wall of the sleeve, a current length of the driving branch chain is read through the indicating rod, a sleeve threaded hole is provided at the lower end of the sleeve, the sleeve threaded hole is in threaded connection with an upper threaded shaft provided at the upper end of a force sensor, the lower threaded shaft provided at the lower end of the force sensor is in threaded connection with the threaded hole formed in the middle of the top surface of the second connecting seat of the distal Hook hinge, and the threaded rod provided in the middle of the bottom surface of the first connecting seat of the distal Hook hinge is inserted into an installing hole of the distal ring and locked and fixed on the distal ring through a nut; each driving branch chain is connected with a driving device, and a rotating output end of the driving device is inserted into an upper end D-shaped hole of the D-shaped shaft sleeve and the two are tightly matched to drive the D-shaped shaft sleeve to rotate.

The present invention has beneficial effects as follows.
1. The electric-manual dual model driving is adopted. The electric mode meets the requirement of high-precision reduction of a fracture operation along a preset trajectory, and the driving is switched into a manual mode after fracture operation, so that the load and economic burden of a patient are reduced and meanwhile the robot has better portability, facilitating the daily activities of the patient.
2. The robot branch chain can be quickly replaced during and after the operation so that the use requirement of special fracture types is met, and the application range of the robot is further expanded.
3. According to the advantages of the six-degree-of-freedom parallel mechanism and the introduction of lightweight materials, the robot body structure has the characteristics of lightweight and high rigidity, and meanwhile, a mode of driving the Hooke hinge is adopted so that the robot branch chain structure is light and has excellent wearability.
4. The integration of fracture reduction and rehabilitation can be realized: firstly, the robot can realize a high-precision fracture reduction process according to a planned trajectory, secondly, stress stimulus can be applied to the broken end of the fracture to promote the bone healing process through the fine adjustment of the pose of the moving platform of the robot, and a force sensor is used for detecting the force of the branch chain so that real-time monitoring can be provided for the whole process, and an accurate and safe fracture rehabilitation process is realized.

BRIEF DESCRIPTION OF THE DRAWINGS

FIG. 4 (*b*) is a schematic diagram of a ¼ cross-section of a platform connecting sleeve of a first driving branch chain of the present invention;

FIG. 6 (*b*) is a schematic diagram of a ¼ cross section of a Hooke hinge center cross of a driving branch chain of a robot of the present invention;

FIG. 7 (*b*) is a schematic diagram of a robot of the present invention in a manual mode switching.

DETAILED DESCRIPTION OF THE PRESENT INVENTION

Preferred embodiments of the invention are described in further detail below.

In order to further understand the content, features, and effects of the present invention, the following embodiments are given as examples, and are described in detail in conjunction with the accompanying drawings as follows.

Figure 1:
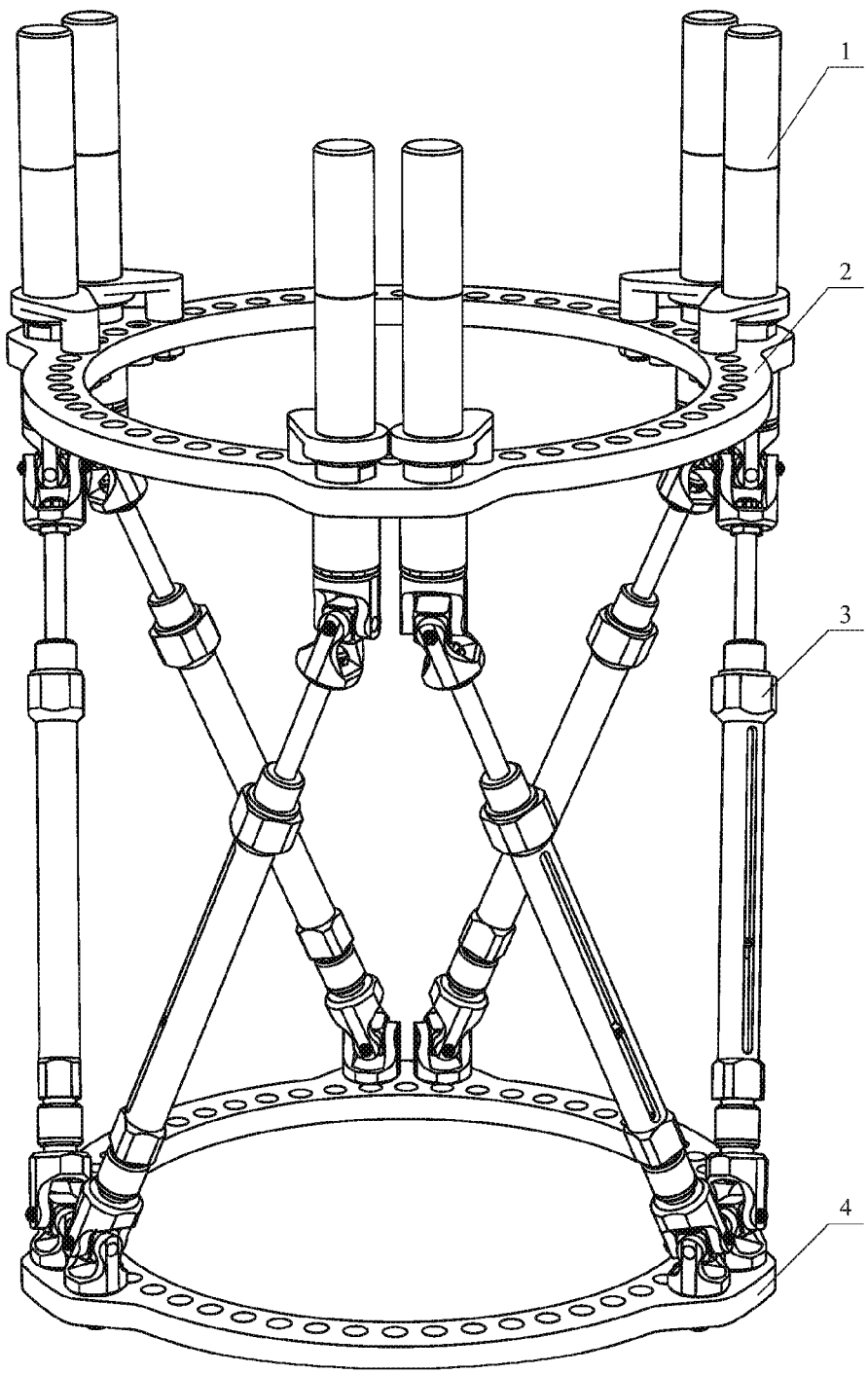
FIG. 1 is a schematic diagram of a wearable robot for integrated fracture reduction and rehabilitation of the present invention in an electric mode.
Figure 2:
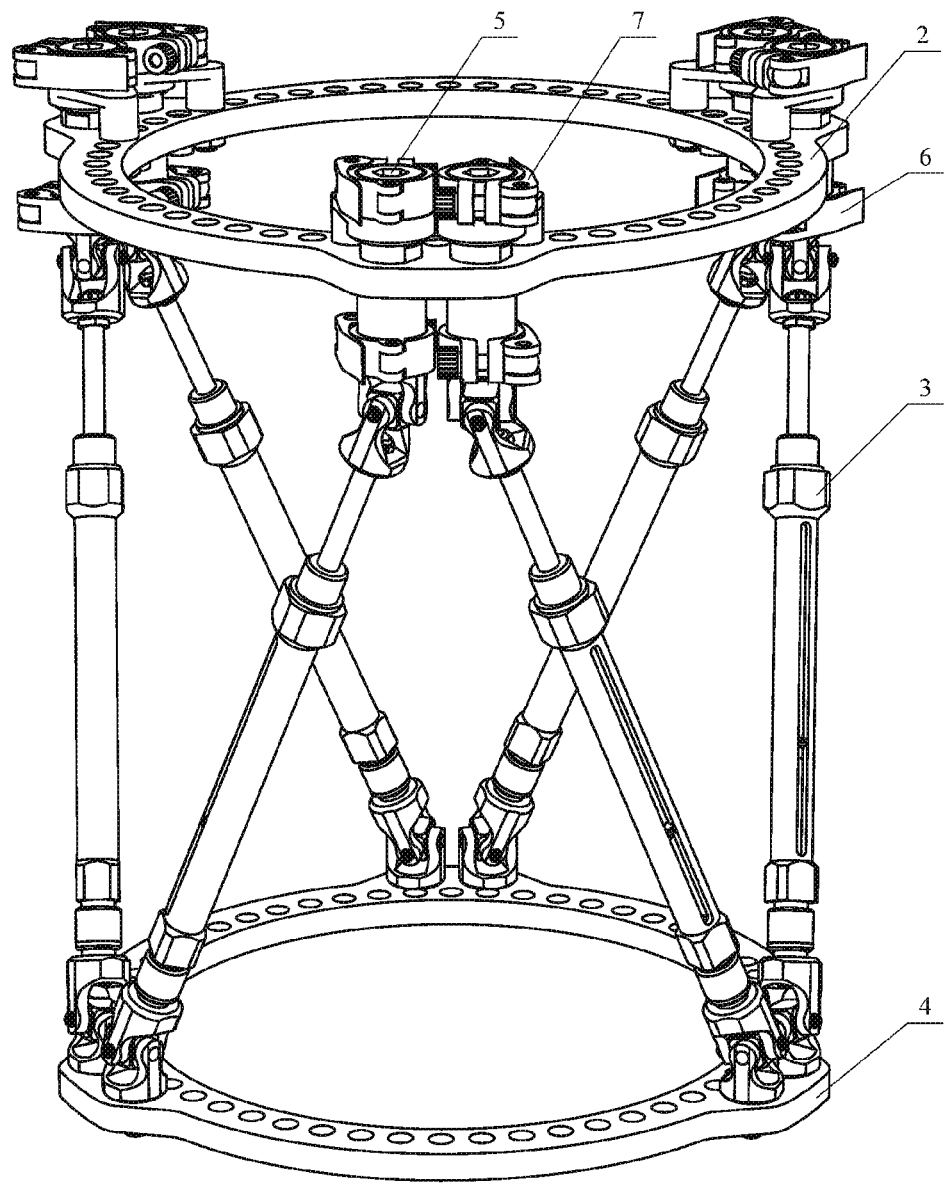
FIG. 2 is a schematic structural view of a wearable robot for integrated fracture reduction and rehabilitation of the present invention in a manual mode.

As shown in FIGS. 1, 2, the wearable robot for integrated fracture reduction and rehabilitation of the invention includes a proximal ring 2 and a distal ring 4 provided below the proximal ring 2. The proximal ring 2 and the distal ring 4 are connected through six driving branch chains 3.

The proximal ring 2 and the distal ring 4 both include annular bodies and are in a central symmetrical structure. Flanges are formed on the annular bodies of the proximal ring 2 and the distal ring 4 by protruding outwards at the outer edges of the annular bodies every 120°, and two installing holes for connecting the driving branch chain 3 are formed at the outer side of each flange in the vertical direction. The proximal ring 2 and the distal ring 4 may be full rings or split rings in ⅔ full circle (i.e., a 120° opening, C-shaped, not necessarily closed), fabricated from lightweight materials (e.g., carbon fibers, etc.). A plurality of round holes with axes thereof provided in the vertical direction is uniformly spaced circumferentially on the inner side of the proximal ring 2 and the distal ring 4 respectively.

The six driving branch chains 3 are identical in structure, the six driving branch chains 3 are divided into two groups according to different included angles with the symmetrical central line of the proximal ring, and the included angles between the two groups of driving branch chains 3 and the symmetrical central line of the proximal ring are equal in magnitude and opposite in direction. Each group of the driving branch chain 3 is uniformly distributed in space by taking the symmetrical central line of the proximal ring as a central axis.

One end is connected with two installing holes of any group of installing holes on the proximal ring, and the other end of the two driving branch chains 3 is connected with two installing holes adjacent to each other in two groups of installing holes on the distal ring.

Figure 3:
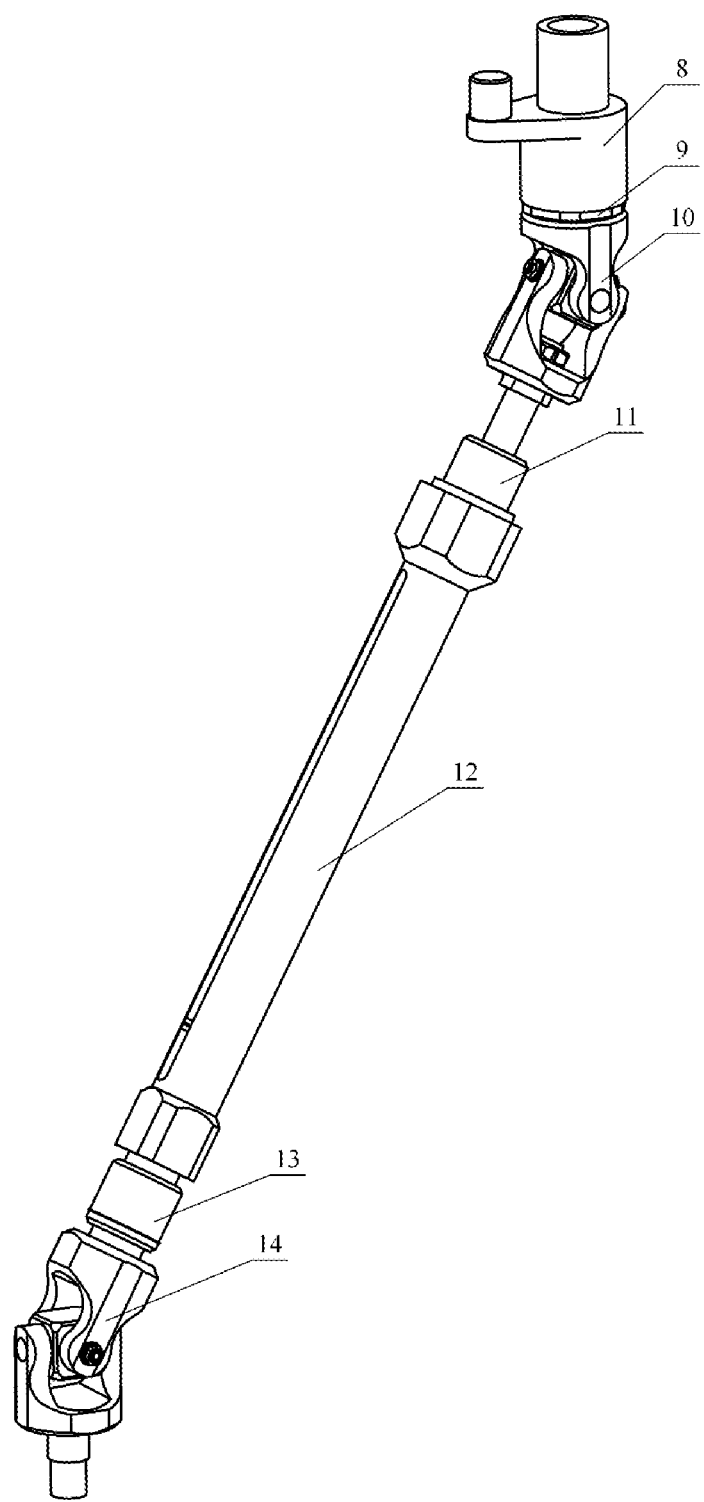
FIG. 3 is a schematic diagram of a first driving branch chain of the present invention.
Figure 4A:
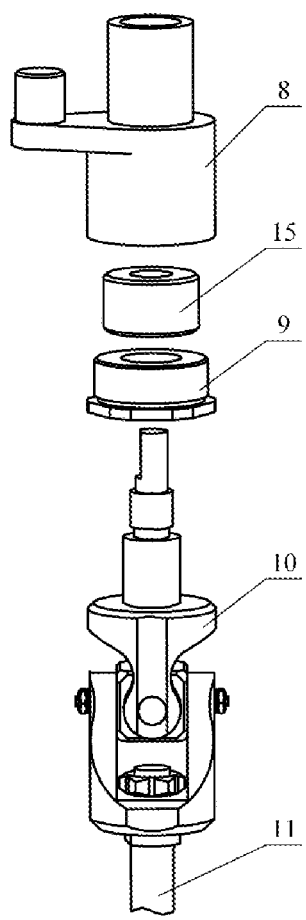
FIG. 4 (*a*) is a schematic diagram of a first driving branch chain of the present invention when a sliding bearing thereof is being installed.
Figure 4B:
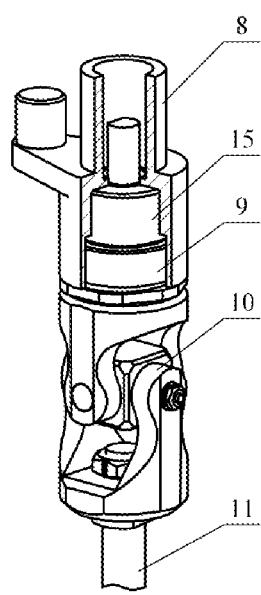
Figure 5:
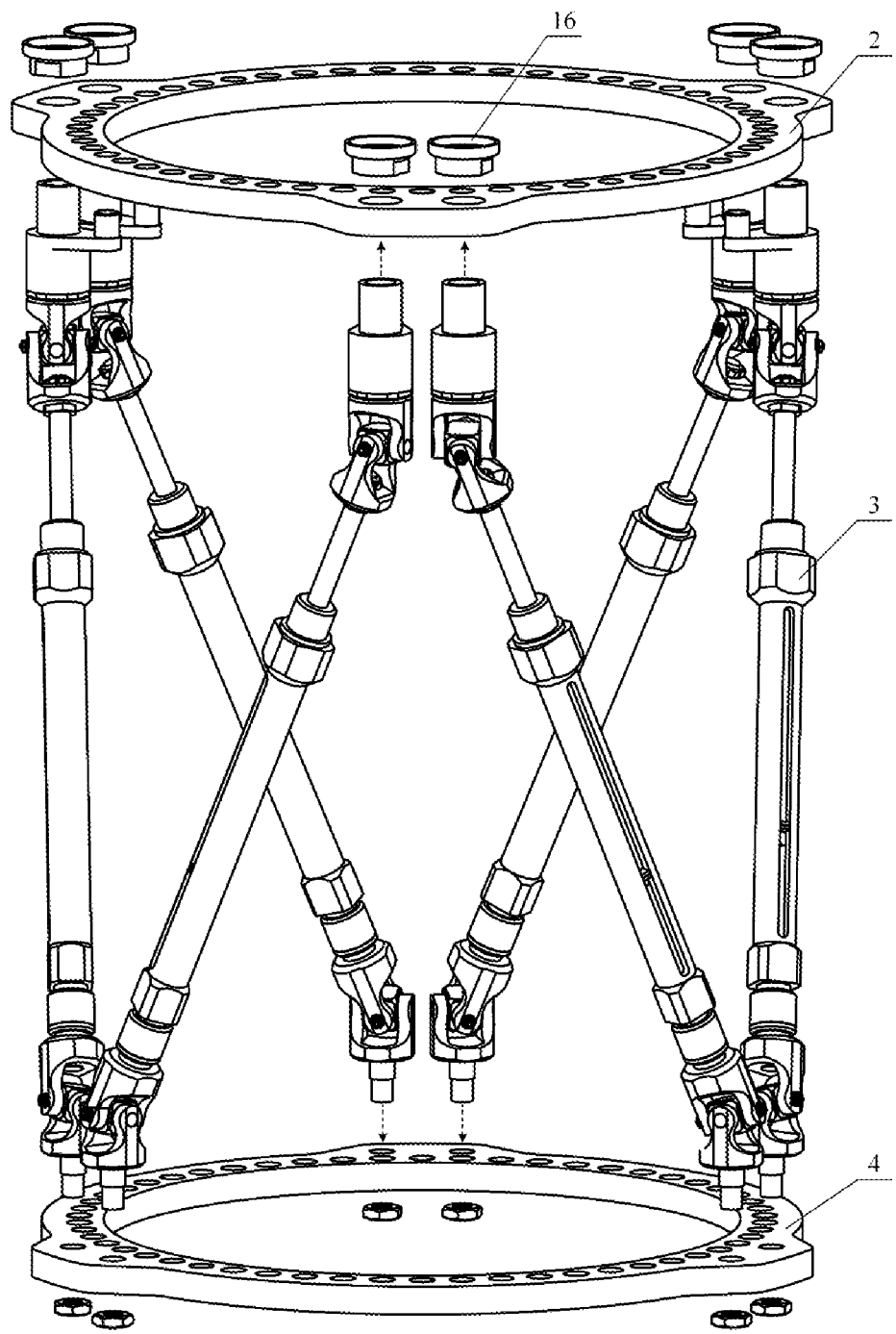
FIG. 5 is a schematic view of a driving branch chain of the present invention when installed.

As shown in FIGS. 3 to 5, each driving branch chain 3 includes a platform connecting sleeve 8, and the platform connecting sleeve 8 includes a lower annular cylinder and an upper annular cylinder which are provided as an integrated upper and lower structure with the same axial line. A supporting arm is provided at the reducing position of the lower annular cylinder and the upper annular cylinder along the horizontal direction, and a directional shaft with the axis thereof provided along the vertical direction is provided on the supporting arm. The upper annular cylinder of the platform connecting sleeve 8 is inserted into one installing hole of the proximal ring 2, the upper annular cylinder is in threaded connection with a central threaded through-hole of the connecting sleeve fastener 16 through external threads provided on the outer wall of the upper annular cylinder 8, and the connecting sleeve fastener 16 is provided as being tightly pressed on the top wall of the proximal ring 2. The connecting sleeve fastener 16 is axially fixed with the proximal ring 2 through threaded connection, and the directional shaft is inserted into the round hole of the proximal ring 2 to limit the axial rotation of the platform connecting sleeve 8.

Both the platform connecting sleeve 8 and the connecting sleeve fastener 16 are fabricated from lightweight materials (such as 7075 aluminum, etc.).

Preferably, two symmetrical and parallel planes are provided on the left side wall and the right side wall of the connecting sleeve fastener 16 to facilitate the clamping of the wrench.

Figure 6A:
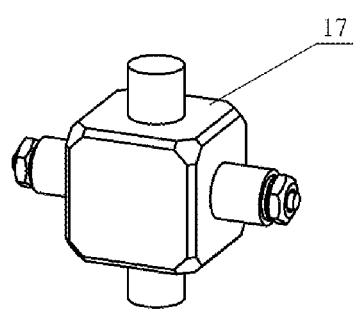
FIG. 6 (*a*) is a schematic diagram of a Hooke hinge center cross of a driving branch chain of a robot of the present invention.
Figure 6B:
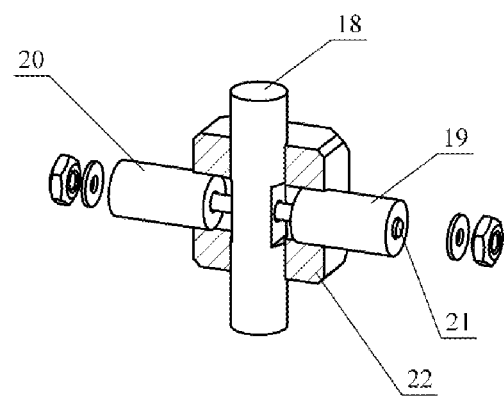

As shown in FIG. 6, the proximal Hooke hinge 10 and the distal Hooke hinge 14 include a central cross structure 17. The central cross structure 17 includes a Hooke hinge central block 22, and a first through-hole and a second through-hole are respectively formed in the middle of the Hooke hinge central block 22 along the cross direction. A long shaft 18 is rotatably connected with the first through-hole. A stud 21 sequentially passes through an axial through-hole in the first short shaft 19, a radial through-hole in the radial middle of the long shaft and an axial through-hole in the second short shaft 20, and the first short shaft 19 and the second short shaft 20 are respectively in rotating fit with the second through-hole. The outer ends of the first short shaft 19 and the second short shaft 20 are respectively inserted into the through-holes of the left connecting arm and the right connecting arm of the U-shaped second connecting seat, the first short shaft 19 and the second short shaft 20 are in rotating fit with the through-holes of the left connecting arm and the right connecting arm of the second connecting seat, and the first short shaft 19 and the second short shaft 20 are tightly pressed on the side wall of the long shaft 18 through nuts and gaskets which are in threaded connection with the two ends of the stud 21. Two ends of the long shaft 18 are respectively inserted into the through-holes of the left connecting arm and the right connecting arm of the U-shaped first connecting seat, and the long shaft is in rotating fit with the through-holes of the left connecting arm and the right connecting arm of the first connecting seat. The stud 21 and the gaskets and nuts connected at the two ends limit the first short shaft 19, the second short shaft 20 and the long shaft 18 from falling out of the first connecting seat and the second connecting seat. The top wall of the first connecting seat of the proximal Hooke hinge 10 is an annular wall.

Both the proximal Hooke hinge 10 and the distal Hooke hinge 14 are fabricated from lightweight materials (such as 7075 aluminum, etc.).

Preferably, the outer portions of the axial through-holes of the first short shaft 19 and the second short shaft 20 are internally threaded holes. After the ordinary gaskets and nuts at both ends of the stud 21 and the stud 21 are dismantled, ordinary bolts and other tools that match the internally threaded holes can be screwed in and the short shaft can be pulled out. After the short shaft is pulled out, the whole Hooke hinge can be divided into two halves. In this way, the simple disassembly of the Hooke hinge is achieved, so that the replacement of different types of the driving branches 3 can be achieved.

One shaft rod is fixed at the center of the top surface of the first connecting seat of the proximal Hooke hinge 10, the lower part of the shaft rod is a cylindrical shaft section, the middle part of the shaft rod being a threaded shaft section and the upper part of the shaft rod being a D-shaped shaft section, and the shaft rod sequentially passes through the central hole of the bearing locking nut 9 and the central threaded through-hole of the sliding bearing 15 from bottom to top. The threaded shaft section in the middle of the shaft rod is in threaded connection and fixation with the central threaded through-hole of the sliding bearing 15, the bearing locking nut 9 is sleeved on the cylindrical shaft section, the diameter of the central hole of the bearing locking nut 9 is larger than that of the cylindrical shaft section of the lower part of the shaft rod, and the bearing locking nut is used for limiting the sliding bearing 15 from falling out.

The bearing locking nut 9 and the sliding bearing 15 are embedded into the central hole of the lower annular cylinder of the platform connecting sleeve 8. The bearing locking nut 9 is in threaded fixation and connection with the inner thread of the central hole of the lower annular cylinder through the outer thread provided on the outer wall of the bearing locking nut 9, and the sliding bearing 15 is axially limited. The sliding bearing 15 is in rotating fit with the central hole of the lower annular cylinder, and the lower end of one D-shaped shaft sleeve 25 passes through the central hole of the upper annular cylinder of the platform connecting sleeve 8 and is tightly sleeved on the D-shaped shaft section at the upper part of the shaft rod. The D-shaped shaft sleeve 25 is in the central hole of the upper annular cylinder of the platform connecting sleeve 8 without contact, that is, clearance fit.

The bearing locking nut 9 and the sliding bearing 15 are fabricated from lightweight materials (such as 7075 aluminum, etc.).

An intermediate prismatic pair 11 includes a lead screw or a ball screw and a flange nut connected to the lead screw or the ball screw through the lead screw pair. One end of the lead screw or the ball screw is in threaded connection with a threaded hole formed in the middle of the bottom surface of the second connecting seat on the proximal Hooke hinge 10, and fixed through a nut. A sleeve 12 is in threaded connection with the flange nut, a sliding groove is formed in the side wall of the sleeve 12 along the axial direction of the sleeve, an indicating rod is connected to the other end of the lead screw or the ball screw, and the indicating rod is inserted into the sliding groove and can move along the sliding groove. A scale is marked on the outer wall of the sleeve 12, and the current length of the driving branch chain 3 is read through the indicating rod. The lead screw or the ball screw of the intermediate prismatic pair 11 rotates, and according to the principle of the lead screw pair and the ball screw pair, the rotating motion output by the driving device is converted into the linear motion of the flange nut in the intermediate prismatic pair 11. The lower end of the sleeve 12 is provided with a sleeve threaded hole, the sleeve threaded hole is in threaded connection with an upper threaded shaft provided at the upper end of the force sensor 13, and the lower threaded shaft provided at the lower end of the force sensor 13 is in threaded connection with a threaded hole formed in the middle of the top surface of the second connecting seat of the distal Hooke hinge 14. A threaded rod provided in the middle of the bottom surface of the first connecting seat of the distal Hooke hinge 14 is inserted into an installing hole on the distal ring 4 and locked and fixed on the distal ring 4 through a nut.

The sleeve 12 is fabricated from a lightweight material (such as 7075 aluminum, etc.).

Each driving branch chain 3 is connected with a driving device, the rotating output end of the driving device is inserted into the upper D-shaped hole of the D-shaped shaft sleeve 25 and the two are tightly matched to drive the D-shaped shaft sleeve 25 to rotate. The proximal Hooke hinge 10 freely rotates relative to the platform connecting sleeve 8 under the action of the electric driving device 1 or the manual driving device 5.

Figure 7A:
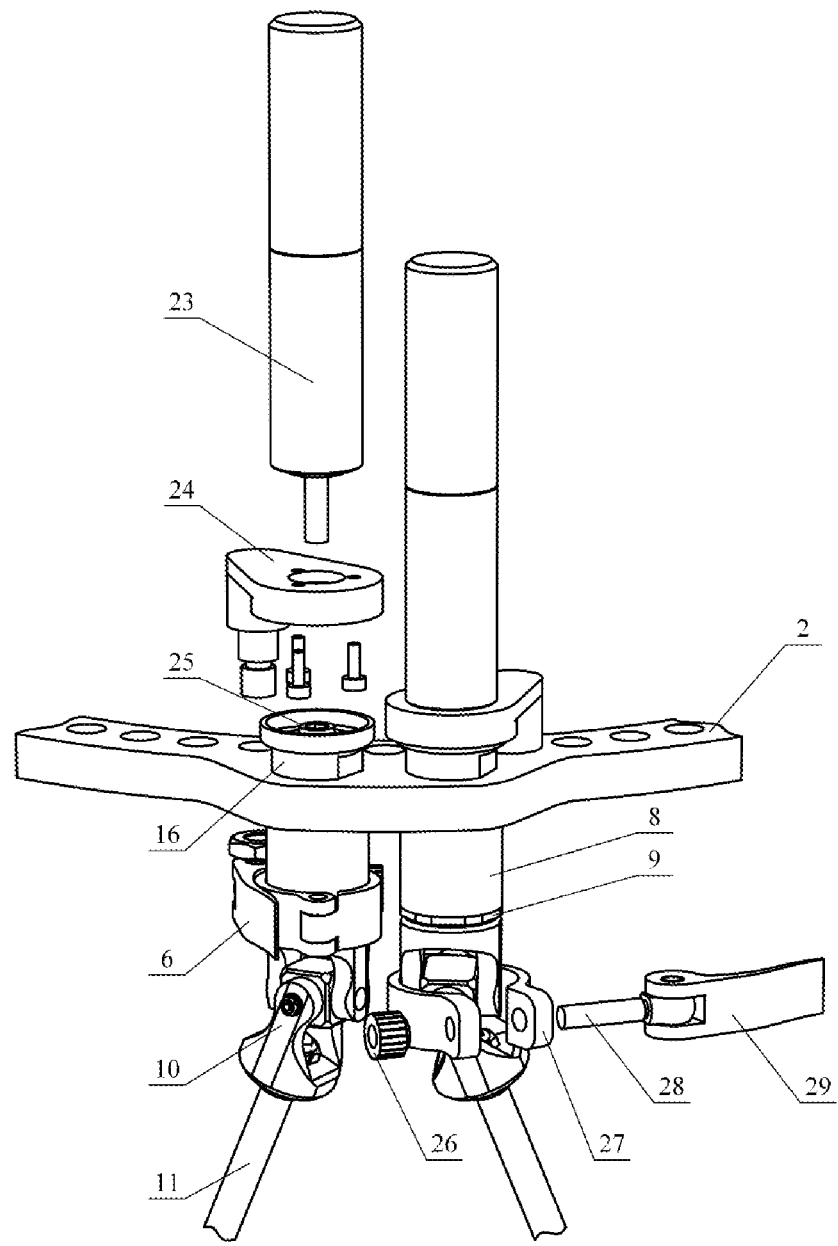
FIG. 7 (*a*) is a schematic diagram of a robot of the present invention when the motor is dismantled.

As shown in FIG. 7a, the driving device is a motor driving device 1. In the electric mode, the motor driving device 1 includes a motor, and one motor 23 is fixedly connected with a motor-platform adapter 24 through a bolt. One side of the bottom wall of the motor-platform adapter 24 is fixedly arranged with a lower end shaft section with external threads, and the lower end shaft section is inserted into a round hole of the proximal ring 2 and is fixedly connected with the proximal ring 2 through a nut. The output shaft of the motor 23 is a D-shaped output shaft, and the D-shaped output shaft is inserted into the upper end D-shaped hole of the D-shaped shaft sleeve 25 and the two are tightly matched. Under the driving of the motor 23, the D-shaped output shaft of the motor rotates, the whole proximal Hooke hinge 10 and the lead screw or the ball screw in threaded connection with the proximal Hooke hinge 10 are driven to rotate through the D-shaped shaft sleeve 25. The flange nut and the sleeve 12 in threaded connection with the flange nut linearly move along the axial direction of the lead screw or the ball screw according to the principle of the lead screw pair or the ball screw pair, and the position of the flange nut and the sleeve 12 relative to the proximal Hooke hinge 10 is adjusted, so that the length of the driving branch chain 3 is adjusted, and six driving branch chains 3 mutually cooperate to realize the spatial 6-degree-of-freedom motion of the distal ring 4 relative to the proximal ring 2.

The proximal Hooke hinge 10 is rotatable relative to the platform connecting sleeve 8. Both the motor-platform adapter 24 and the D-shaped shaft sleeve 25 are fabricated from lightweight materials (such as 7075 aluminum, etc.).

Figure 7B:
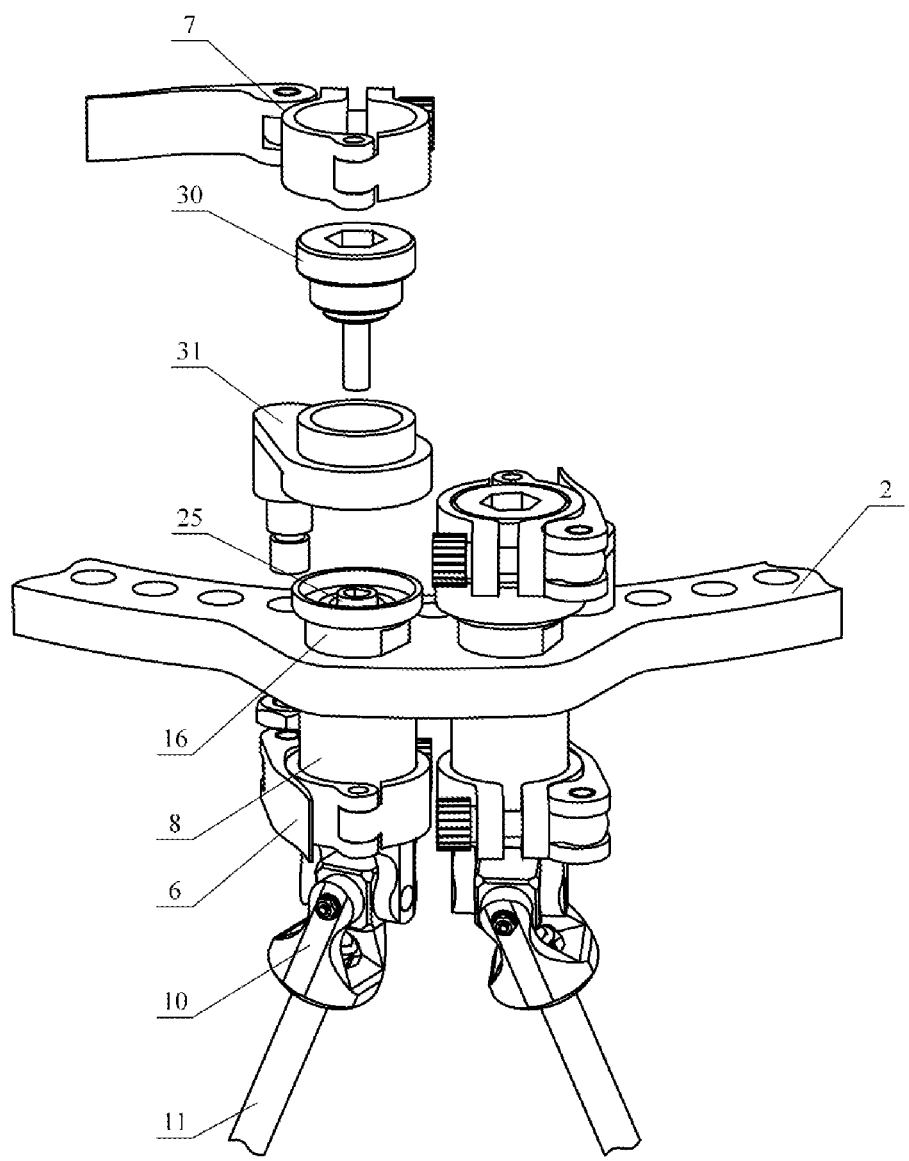

As shown in FIG. 7b, the driving device is a manual driving device 5. In a manual mode, the manual driving device 5 includes a manual-platform adapter 31, a lower end shaft section with external threads is fixed on one side of the bottom wall of the manual-platform adapter 31, and the lower end shaft section is inserted into a round hole of the proximal ring 2 and is connected and fixed with the proximal ring 2 through a nut. A platform adapter annular boss is provided on the top wall of the manual-platform adapter 31, a rotating shaft annular boss, a cylindrical surface shaft section and a D-shaped shaft section are sequentially provided on the manual rotating shaft 30 from top to bottom, a through-hole coaxial with the platform adapter annular boss is formed in the manual-platform adapter 31, and a lower end D-shaped shaft section of the manual rotating shaft 30 passes through the annular hole of the platform adapter annular boss and the through-hole of the manual-platform adapter 31 to be inserted into the upper end D-shaped hole of the D-shaped shaft sleeve 25 and the two are tightly matched. The cylindrical surface shaft section of the manual rotating shaft 30 is in clearance fit with the annular hole of the platform adapter annular boss and can freely rotate. The rotating shaft annular boss is supported on the platform adapter annular boss and the two have the same outer diameter.

Both the manual-platform adapter 31 and the manual rotating shaft 30 are fabricated from lightweight materials (such as 7075 aluminum, etc.).

Further, since only the output shaft of the motor is rotating, the motor body can be directly connected and fixed to the motor-platform adapter 24 through a bolt. Here, the manual rotating shaft 30 needs to be rotated, so it is simply inserted into the through-hole of the manual-platform adapter 31, and then the two are locked by means of a first locking clip 7 (FIG. 7b). The manual driving device 5 includes a first locking clip 7.

The first locking clip 7 includes a locking ring 27, and the locking ring 27 is of an open annular structure and consists of two halves. The butt joint of the two halves of open rings can be rotatably connected through a rotating shaft provided in the vertical direction, and a lifting lug structure extends at the opening of the locking ring 27. One end of the locking clip bolt 28 passes through the lifting lug hole of the locking ring 27 and is in threaded connection with the locking clip nut 26. The other end of the locking clip bolt 28 is rotatably connected with one end of the locking clip wrench 29 through a cylindrical pin with an axis parallel to the axis of the locking ring 27. The first locking clip 7 is used for hooping the outer walls of the platform adapter annular boss and the rotating shaft annular boss and enabling the locking clip wrench to be attached to the outer wall of the locking ring 27 by rotating the locking clip wrench 29.

The first locking clip 7 is fabricated from lightweight materials (such as 7075 aluminum, etc.).

The first locking clip 7 locks the manual rotating shaft 30 and the manual-platform adapter 31 to limit the rotation of the manual rotating shaft 30 relative to the manual-platform adapter 31. An inner hexagonal hole is formed in the top of the manual rotating shaft 30, and a tool such as an inner hexagonal wrench can be used for manually driving the proximal Hooke hinge 10 to rotate relative to the platform connecting sleeve 8. In the manual mode, by replacing the motor 23 and the motor-platform adapter 24 in the electric mode with the manual rotating shaft 30 and the manual-platform adapter 31, respectively, the switching from the electric mode to the manual mode can be achieved, and the process is reversible.

When the electric mode is converted into the manual mode, the proximal Hooke hinge 10 and the platform connecting sleeve 8 need to be locked, so that the rotation of the proximal Hooke hinge 10 relative to the platform connecting sleeve 8 is limited. The rotation limiting device can adopt an existing device or can adopt a second locking clip 6 with the same structure as that of the first locking clip 7. The locking ring 27 is used for hooping the annular wall of the first connecting seat of the proximal Hooke hinge 10 and the lower annular cylinder of the platform connecting sleeve 8 and enabling the locking clip wrench to be attached to the outer wall of the locking ring 27 by rotating the locking clip wrench 29. The outer diameter of the annular wall of the first connecting seat of the proximal Hooke hinge 10 is the same as the outer diameter of the lower annular cylinder of the platform connecting sleeve 8 so as to ensure the locking effect of the second locking clip 6 (the diameters of the two pieces are the same as the inner diameter of the locking ring of the locking clip so as to provide a better locking effect). After the electric-manual mode conversion is completed, the second locking clip 6 is dismantled.

When the electric mode is switched to the manual mode, in order to avoid the change of the length of the driving branch chain 3 caused by the rotation of the proximal Hooke hinge 10 in the process of disassembling the motor driving device 1, the proximal Hooke hinge 10 and the platform connecting sleeve 8 need to be firstly locked by the second locking clip 6. During locking, firstly, the locking ring 27 is sleeved between the proximal Hooke hinge 10 and the platform connecting sleeve 8, then one end of the locking clip bolt 28 passes through the lifting lug hole of the locking ring 27, then the locking clip nut 26 is used for pretightening, then the locking clip wrench 29 is closed, and the opening of the locking ring 27 is contracted through the eccentric structure of the locking clip wrench 29 so that the proximal Hooke hinge 10 and platform connecting sleeve 8 are thereby tightly locked. In both the electric mode and the manual mode, the driving device (including the motor driving device 1 in the electric mode and the manual driving device 5 in the manual mode) drives the lead screw or the ball screw of the intermediate prismatic pair 11 to rotate through the proximal Hooke hinge 10. According to the principle of the lead screw pair or the ball screw pair, the rotary motion output by the driving device is converted into the linear motion of the flange nut in the intermediate prismatic pair 11 and the sleeve 12 in threaded connection with the flange nut in the axial direction of the lead screw or the ball screw, so that the position of the flange nut and the sleeve 12 relative to the proximal Hooke hinge 10 is adjusted, and the length of the driving branch chain 3 is further adjusted. By varying the lengths of the six driving branch chains 3, a spatial six-degree-of-freedom motion of the distal ring 4 relative to the proximal ring 2 can be achieved.

In the fracture reduction operation process, the two ends of the fractured bone are respectively fixedly connected with the distal ring 4 and the proximal ring 2 by using a semi-spiral pin or a Kirschner wire, and then the motion trajectory of the center of the distal ring 4 relative to the center of the proximal ring 2 in the fracture reduction process is acquired by using an existing medical means or referring to a posture recognition and reduction method described in patents CN109009376A and CN108742804A. Furthermore, a length adjustment scheme of the six driving branch chains 3 is obtained through preoperative planning, and finally the six driving branch chains 3 are driven by the motor 23, so that the high-precision fracture reduction according to a planned trajectory is realized. At the same time, referring to the fracture rehabilitation evaluation method described in the patent CN109077785A, the force sensor 13 is used for detecting the change condition of the force of the driving branch chain 3, and the safety of the whole fracture reduction operation process is ensured by setting an emergency stop threshold value of the force of the branch chain in the operation. In the fracture rehabilitation process, according to the robot of the invention, the length of the six driving branch chains 3 can be finely adjusted through the motor so that the pose of the distal ring 4 can be finely adjusted. Stress stimulus is applied to the broken end of the fracture to promote the bone healing process, and meanwhile, the force sensor 13 is utilized to provide real-time monitoring for the whole process. Therefore, the wearable robot for integrated fracture reduction and rehabilitation herein can meet the integrated realization of fracture reduction surgery and fracture rehabilitation.

According to the wearable robot for integrated fracture reduction and rehabilitation of the invention, a large amount of lightweight materials (such as carbon fiber, 7075 aluminum and the like) are used for parts and components, and structural parameters of the wearable robot for integrated fracture reduction and rehabilitation are obtained through optimization design, so that the robot body structure has low weight and high rigidity. Meanwhile, the mode of driving the proximal Hooke hinge 10 is adopted, so that the six driving branch chains 3 of the robot are compact in layout, light in structure and excellent in wearability.

Besides, the wearable robot for integrated fracture reduction and rehabilitation of the invention also has an electric-manual conversion function. The electric mode can meet the requirement of high-precision reduction of a fracture operation along a preset trajectory, and the robot can be switched into a manual mode in a postoperative fracture rehabilitation stage, so that the robot has better portability while reducing the load of a patient and the medical cost, and is more beneficial to the daily activities of the patient. When the rehabilitation exercise is performed, the robot can be switched into the electric mode again, so that the adjustment requirement of the fracture rehabilitation process can be met, and the rehabilitation exercise can be performed more reasonably. Meanwhile, the proximal Hooke hinge 10 and the distal Hooke hinge 14 on the driving branch chain 3 of the robot can be quickly disassembled and assembled, and different types of the driving branch chains 3 can be quickly replaced in operation and after operation according to different use requirements so as to meet the use requirements of different types of fractures and expand the application range of the robot.

The above description of the present invention is intended to be merely illustrative, and not restrictive. Therefore, preferred embodiments of the present invention are not limited to the preferred embodiments described above. If a person of ordinary skills in the art receives its enlightenment and does not deviate from the purpose of the present invention and the scope of the claims, other changes or variations shall fall within the scope of the present invention.

What is claimed is:

1. A wearable robot for integrated fracture reduction and rehabilitation, comprising a proximal ring (2) and a distal ring (4) provided below the proximal ring, wherein the proximal ring and the distal ring are connected through six driving branch chains (3), wherein:

the proximal ring and the distal ring both comprise annular bodies and are in a central symmetrical structure, flanges are formed on the annular bodies of the proximal ring and the distal ring by protruding outwards at outer edges of the annular bodies every 120°, two installing holes for connecting the driving branch chains are formed at the outer side of each flange in a vertical direction, and a plurality of round holes with axes provided along the vertical direction is uniformly spaced on the inner side of the proximal ring and the distal ring along a circumferential direction respectively;

the six driving branch chains (3) are identical in structure, the six driving branch chains are divided into two groups according to different included angles with a symmetrical central line of the proximal ring, the included angles between two groups of driving branch chains and the symmetrical central line of the proximal ring are equal in magnitude and opposite in direction, and each group of the driving branch chains is uniformly distributed in space by taking the symmetrical central line of the proximal ring as a central axis;

one end is connected with two installing holes of any group of installing holes on the proximal ring, and the other end of the two driving branch chains (3) is connected with two installing holes adjacent to each other in two groups of installing holes on the distal ring;

each of the driving branch chains (3) comprises a platform connecting sleeve (8), the platform connecting sleeve comprises a lower annular cylinder and an upper annular cylinder which are provided as an integrated upper and lower structure with a same axial line, one supporting arm is provided at a reducing position of the lower annular cylinder and the upper annular cylinder along a horizontal direction, a directional shaft with an axis thereof provided along the vertical direction is provided on the supporting arm, the upper annular cylinder of the platform connecting sleeve is inserted into one installing hole of the proximal ring (2), the upper annular cylinder is in threaded connection with a central threaded through-hole of a connecting sleeve fastener (16) through an external thread provided on an outer wall of the upper annular cylinder, the connecting sleeve fastener is provided as being tightly pressed on a top wall of the proximal ring (2), and the directional shaft is inserted into a round hole of the proximal ring to limit an axial rotation of the platform connecting sleeve (8);

a proximal Hooke hinge (10) and a distal Hooke hinge (14) comprise a central cross structure (17), the central cross structure (17) comprises a Hooke hinge central block (22), a first through-hole and a second through-hole are respectively formed in a middle of the Hooke hinge central block along a cross direction, one long shaft (18) is rotatably connected with the first through-hole, a stud (21) sequentially passes through an axial through-hole in a first short shaft (19), and a radial through-hole in a radial middle of the long shaft and an axial through-hole in a second short shaft (20), and the first short shaft (19) and the second short shaft (20) are respectively in rotating fit with the second through-hole; outer ends of the first short shaft and the second short shaft are respectively inserted into through-holes of a left connecting arm and a right connecting arm of an U-shaped second connecting seat, the first short shaft and the second short shaft are in rotating fit with the through-holes of the left connecting arm and the right connecting arm of the second connecting seat, the first short shaft and the second short shaft are tightly pressed on a side wall of the long shaft through nuts and gaskets which are in threaded connection with two ends of the stud (21), two ends of the long shaft are respectively inserted into the through-holes of the left connecting arm and the right connecting arm of a U-shaped first connecting seat, the long shaft is in rotating fit with the through-holes of the left connecting arm and the right connecting arm of the first connecting seat (18), and the top wall of the first connecting seat of the proximal Hooke hinge (10) is an annular wall;

one shaft rod is fixed at a center of a top surface of the first connecting seat of the proximal Hooke hinge, a lower part of the shaft rod is a cylindrical shaft section, a middle part of the shaft rod being a threaded shaft section and an upper part of the shaft rod being a D-shaped shaft section, the shaft rod sequentially passes through the central hole of a bearing locking nut and the central threaded through-hole of a sliding bearing from bottom to top, the threaded shaft section in the middle of the shaft rod is in threaded connection and fixation with a central threaded through-hole of the sliding bearing, the bearing locking nut is sleeved on the cylindrical shaft section, and a diameter of the central hole of the bearing locking nut is larger than that of the cylindrical shaft section of the lower part of the shaft rod;

the bearing locking nut (9) and the sliding bearing (15) are embedded into the central hole of the lower annular cylinder of the platform connecting sleeve (8), the bearing locking nut is in threaded fixation and connection with the inner thread of the central hole of the lower annular cylinder through the outer thread provided on the outer wall of the bearing locking nut, the sliding bearing is in rotating fit with the central hole of the lower annular cylinder, the lower end of one D-shaped shaft sleeve (25) passes through the central hole of the upper annular cylinder of the platform connecting sleeve (8) and is tightly sleeved on the D-shaped shaft section at the upper part of the shaft rod, and the D-shaped shaft sleeve is in clearance fit with the central hole of the upper annular cylinder of the platform connecting sleeve;

one intermediate prismatic pair (11) comprises a lead screw or a ball screw and a flange nut connected to the lead screw or the ball screw through a lead screw pair, one end of the lead screw or the ball screw is in threaded connection with a threaded hole in the middle of a bottom surface of a second connecting seat on the proximal Hooke hinge (10) and fixed through a nut, a sleeve (12) is in threaded connection with the flange nut, the side wall of the sleeve is provided with a sliding groove along the axial direction of the sleeve, the other end of the lead screw or the ball screw is connected with an indicating rod, the indicating rod is inserted into the sliding groove and can move along the sliding groove, scales are marked on the outer wall of the sleeve (12), a current length of the driving branch chain (3) is read through the indicating rod, a sleeve threaded hole is provided at the lower end of the sleeve, the sleeve threaded hole is in threaded connection with an upper threaded shaft provided at the upper end of a force sensor (13), a lower threaded shaft provided at the lower end of the force sensor is in threaded connection with the threaded hole formed in the middle of the top surface of the second connecting seat of the distal Hooke hinge (14), and the threaded rod provided in the middle of the bottom surface of the first connecting seat of the distal Hooke hinge is inserted into an installing hole of the distal ring and locked and fixed on the distal ring through a nut; each driving branch chain is connected with a driving device, and a rotating output end of the driving device is inserted into an upper end D-shaped hole of the D-shaped shaft sleeve (25) and the two are tightly matched to drive the D-shaped shaft sleeve to rotate.

2. The wearable robot for integrated fracture reduction and rehabilitation according to claim 1, wherein the driving device is a motor driving device (1), the motor driving device comprises a motor, the motor (23) is connected and fixed with a motor-platform adapter (24) through a bolt, a lower end shaft section with external threads is fixed on one side of a bottom wall of the motor-platform adapter, the lower end shaft section is inserted into the round hole of the proximal ring (2) and is connected and fixed with the proximal ring through a nut, the output shaft of the motor is a D-shaped output shaft, and the D-shaped output shaft is inserted into the upper end D-shaped hole of the D-shaped shaft sleeve (25) and the two are tightly matched.

3. The wearable robot for integrated fracture reduction and rehabilitation according to claim 2, wherein two planes that are symmetrically parallel are provided on a left side wall and a right side wall of the connecting sleeve fastener.

4. The wearable robot for integrated fracture reduction and rehabilitation according to claim 1, wherein the driving device is a manual driving device (5), the manual driving device comprises a manual-platform adapter (31), the lower end shaft section with external threads is fixed on one side of a bottom wall of the manual-platform adapter, the lower end shaft section is inserted into the round hole of the proximal ring (2) and is connected and fixed with the proximal ring through a nut, a platform adapter annular boss is provided on a top wall of the manual-platform adapter, a rotating shaft annular boss, a cylindrical surface shaft section and a D-shaped shaft section are sequentially provided on a manual rotating shaft (30) from top to bottom, a through-hole coaxial with the platform adapter annular boss is formed in the manual-platform adapter (31), a lower end D-shaped shaft section of the manual rotating shaft passes through an annular hole of the platform adapter annular boss and the through-hole of the manual-platform adapter to be inserted into the upper end D-shaped hole of the D-shaped shaft sleeve (25) and the two are tightly matched, the cylindrical surface shaft section of the manual rotating shaft is in clearance fit with the annular hole of the platform adapter annular boss, the rotating shaft annular boss is supported on the platform adapter annular boss and the two have the same outer diameter, and an inner hexagonal hole is formed at the top of the manual rotating shaft;

one first locking clip (7) comprises a locking ring (27), the locking ring is of an open annular structure and consists of two halves, butt joints of the two halves of the open ring can be rotatably connected through a rotating shaft provided in the vertical direction, a lifting lug structure extends at the opening of the locking ring, one end of a locking clip bolt (28) passes through a lifting lug hole of the locking ring and is in threaded connection with a locking clip nut (26), the other end of the locking clip bolt is rotatably connected with one end of a locking clip wrench (29) through a cylindrical pin with an axis parallel to the axis of the locking ring, the first locking clip (7) is used for hooping the outer walls of the platform adapter annular boss and the rotating shaft annular boss, and the locking clip wrench can be attached to the outer wall of the locking ring by rotating the locking clip wrench.

5. The wearable robot for integrated fracture reduction and rehabilitation according to claim 4, wherein two planes that are symmetrically parallel are provided on a left side wall and a right side wall of the connecting sleeve fastener.

6. The wearable robot for integrated fracture reduction and rehabilitation according to claim 1, wherein two planes that are symmetrically parallel are provided on a left side wall and a right side wall of the connecting sleeve fastener.

7. The wearable robot for integrated fracture reduction and rehabilitation according to claim 6, wherein outer side portions of the axial through-holes of the first short shaft and the second short shaft are internally threaded holes.

8. The wearable robot for integrated fracture reduction and rehabilitation according to claim 7, wherein the proximal ring, the distal ring, the platform connecting sleeve, the connecting sleeve fastener, the sliding bearing, the bearing locking nut, the proximal Hooke hinge, the sleeve, the distal Hooke hinge, the motor-platform adapter, the D-shaped shaft sleeve, the manual-platform adapter, the manual rotating shaft and the first locking clip all are formed from lightweight materials.

\* \* \* \* \*